(12) United States Patent
Yokoyama

(10) Patent No.: US 9,748,012 B2
(45) Date of Patent: Aug. 29, 2017

(54) METHOD FOR MANUFACTURING METAL GRATING STRUCTURE, METAL GRATING STRUCTURE MANUFACTURED BY THE METHOD, AND X-RAY IMAGING DEVICE USING THE METAL GRATING STRUCTURE

(75) Inventor: Mitsuru Yokoyama, Takatsuki (JP)

(73) Assignee: KONICA MINOLTA, INC., Tokyo (JP)

(*) Notice: Subject to any disclaimer, the term of this patent is extended or adjusted under 35 U.S.C. 154(b) by 48 days.

(21) Appl. No.: 13/997,045

(22) PCT Filed: Nov. 16, 2011

(86) PCT No.: PCT/JP2011/006388
§ 371 (c)(1),
(2), (4) Date: Jun. 21, 2013

(87) PCT Pub. No.: WO2012/086121
PCT Pub. Date: Jun. 28, 2012

(65) Prior Publication Data
US 2013/0279651 A1    Oct. 24, 2013

(30) Foreign Application Priority Data

Dec. 21, 2010   (JP) ................................ 2010-284250

(51) Int. Cl.
*G21K 1/06*      (2006.01)
*G21K 1/02*      (2006.01)
*G01N 23/04*     (2006.01)

(52) U.S. Cl.
CPC .............. *G21K 1/06* (2013.01); *G01N 23/04* (2013.01); *G21K 1/02* (2013.01); *G21K 2207/005* (2013.01)

(58) Field of Classification Search
CPC ...... B60K 5/04; B60K 5/1208; B60K 5/1216; B60K 5/1241; G01T 1/24; G21K 1/06;
(Continued)

(56) References Cited

U.S. PATENT DOCUMENTS 4,589,193 A * 5/1986 Goth ................ H01L 21/76237
257/517
5,012,311 A * 4/1991 Shirato ......................... 257/353
(Continued)

FOREIGN PATENT DOCUMENTS

JP     2009-037023     2/2009
JP     2010-185728     8/2010
(Continued)

OTHER PUBLICATIONS

Shi et. al., Improved the Surface Roughness of Silicon Nanophotonic Devices by Thermal Oxidation Method, Nov. 2010, 3rd International Photonics & OptoElectronics Meetings (POEM), vol. 276, p. 1, 3, 4, 5.*

(Continued)

*Primary Examiner* — Glen Kao
(74) *Attorney, Agent, or Firm* — Cozen O'Connor

(57) ABSTRACT

According to a method for manufacturing a metal grating structure of the present invention, in filling a concave portion formed in a silicon substrate (30), for instance, a slit groove (SD) with metal by an electroforming method, an insulating layer (34) is formed in advance on an inner surface of the slit groove (SD) as an example of the concave portion by a thermal oxidation method. Accordingly, the metal grating structure manufacturing method is advantageous in finely forming metal parts of the grating structure. A metal grating structure of the present invention is manufactured by the above manufacturing method, and an X-ray imaging device of the present invention is incorporated with the metal grating structure.

14 Claims, 9 Drawing Sheets

(58) Field of Classification Search
CPC .... G21K 1/02; G21K 2207/005; G01N 23/02; G01N 23/04; G02B 6/13; G02B 6/136; H01L 21/3205; H01L 21/32055; H01L 29/06
USPC ............... 378/34, 35, 36, 145, 147; 216/24; 438/584, 597, 669, 734
See application file for complete search history.

(56) References Cited

U.S. PATENT DOCUMENTS

| | | | | |
|---|---|---|---|---|
| 5,059,549 | A | * 10/1991 | Furuhata | ............ H01L 27/0623 148/DIG. 9 |
| 2011/0031470 | A1 | * 2/2011 | Scherer | ................. B82Y 10/00 257/9 |
| 2011/0168908 | A1 | 7/2011 | Wang et al. | |

FOREIGN PATENT DOCUMENTS

| | | | | |
|---|---|---|---|---|
| JP | 2010185828 | * | 8/2010 | ............ G01N 23/04 |
| JP | 2011-157622 | | 8/2011 | |

OTHER PUBLICATIONS

Ganji et. al., Deep Trenches in Silicon Structure using DRIE Method with Aluminum as an Etching Mask, Dec. 2006, IEEE International Conference on Semiconductor Electronics (ICSE), p. 42.*

Laermer et. al., Bosch deep silicon etching: improving uniformity and etch rate for advanced MEMS applications, Jan. 1999, Twelfth IEEE International Conference on Micro Electro Mechanical Systems (MEMS), p. 211, 212.*

Lehmann et. al., Formation Mechanism and Properties of Electrochemically Etched Trenches in n-Type Silicon, Feb. 1990, J. Electrochem. Soc., vol. 137, No. 2, p. 653, 654.*

Matsumoto et. al., Fabrication of diffraction grating for X-ray Talbot interferometer, Jun. 2006, Microsyst. Technol. vol. 13, p. 543-545.*

J. Ohara, "A New Deep Ion Etching Process by Dual Sidewall Protection Layer", The 13$^{th}$ Annual International Conference on Micro Electro Mechanical Systems (MEMS 2000); vol. 5, No. 1, pp. 45-50, 2000.

Vargas Llona et al., "Seedless electroplating on patterned silicon", Journal of Micromechanics & Microengineering, Institute of Physics Publishing, vol. 16, No. 6, Jun. 1, 2006, pp. S1-S6.

* cited by examiner

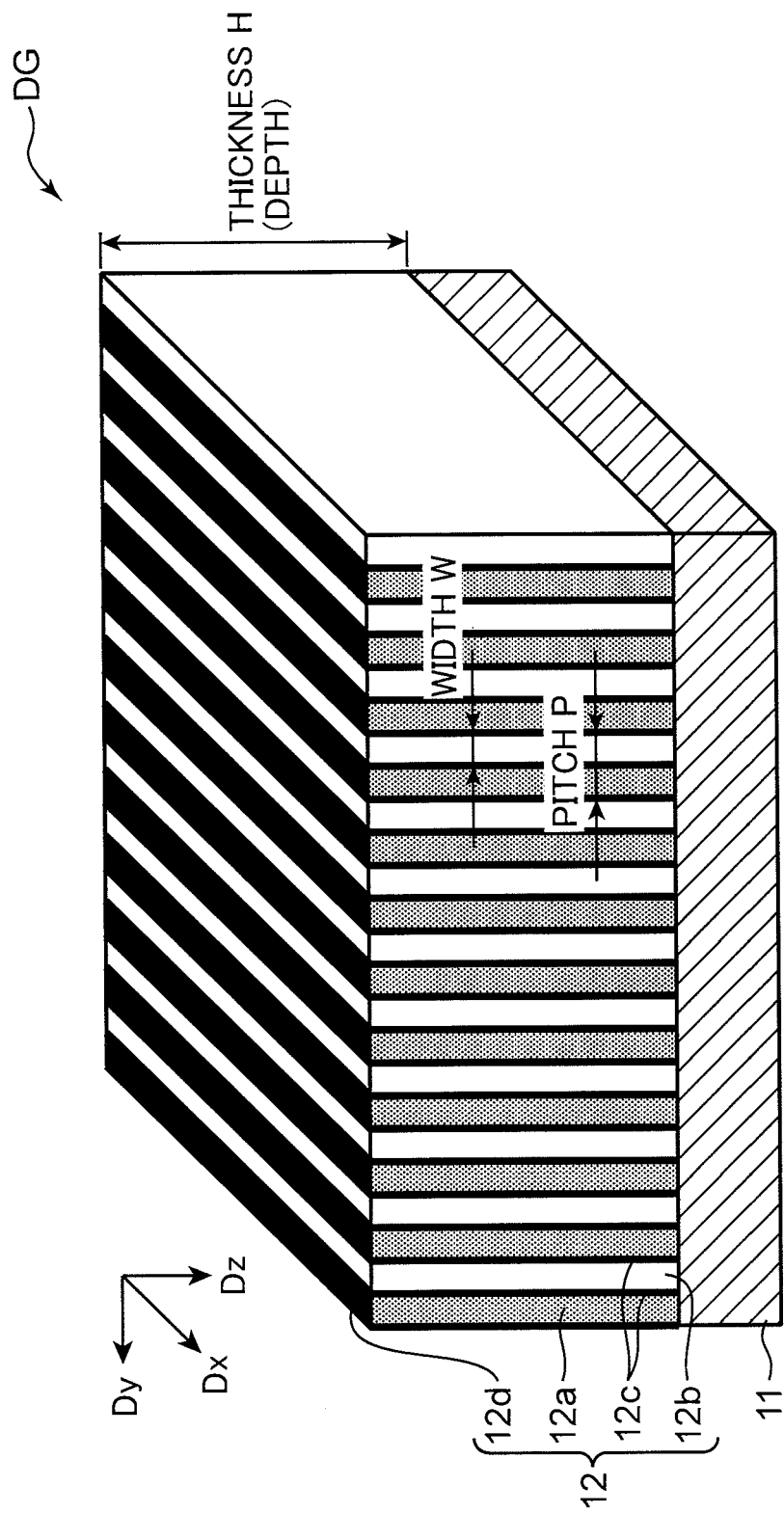

METHOD FOR MANUFACTURING METAL GRATING STRUCTURE, METAL GRATING STRUCTURE MANUFACTURED BY THE METHOD, AND X-RAY IMAGING DEVICE USING THE METAL GRATING STRUCTURE

RELATED APPLICATIONS

This is a U.S. national stage of International application No. PCT/JP2011/006388 filed on Nov. 16, 2011.

This patent application claims the priority of Japanese application no. 2010-284250 filed Dec. 21, 2010, the disclosure content of which is hereby incorporated by reference.

TECHNICAL FIELD

The present invention relates to a method for manufacturing a metal grating structure for manufacturing a grating suitably used for, for instance, a Talbot interferometer or a Talbot-Lau interferometer. The present invention also relates to a metal grating structure manufactured by the manufacturing method, and an X-ray imaging device incorporated with the metal grating structure.

BACKGROUND ART

Diffraction gratings are utilized in optical systems of various devices, as a spectral element provided with multitudes of parallel periodic structures. In recent years, diffraction gratings are also applied to X-ray imaging devices. Diffraction gratings are roughly classified into transmissive diffraction gratings and reflective diffraction gratings according to diffraction methods. The transmissive diffraction gratings include amplitude-type diffraction gratings (absorptive diffraction gratings) in which light absorption parts are periodically arranged on a substrate for transmitting light, and phase-type diffraction gratings in which parts for shifting the phase of light are periodically arranged on a substrate for transmitting light. In the present specification, absorption means light of an amount larger than 50% of the total light amount is absorbed by a diffraction grating, and transmission means light of an amount larger than 50% of the total light amount is transmitted through a diffraction grating.

Diffraction gratings for near infrared light, visible light, or ultraviolet light can be relatively easily manufactured in view of a point that near infrared light, visible light, and ultraviolet light are sufficiently absorbed by a very thin metal film. For instance, forming a metal film on a substrate by metal vapor deposition on the substrate such as a glass plate, and forming the metal film into a grating pattern enables to manufacture an amplitude-type diffraction grating by a metal grating structure. In an amplitude-type diffraction grating for visible light, in the case where aluminum (Al) is used as metal, forming a metal film having a thickness of about 100 nm for instance is sufficient, because the transmittance of visible light (wavelength in the range of from about 400 nm to about 800 nm) through aluminum is 0.001% or less.

On the other hand, as is well known, generally, X-ray has a property that absorption by matter is very low, and the phase shift is not so large. Even in the case where a diffraction grating for X-ray is manufactured with use of gold, which is a preferable material, it is necessary to form a gold film of about 100 µm in thickness. In the case where periodic structures are formed, with light transmissive parts and light absorption parts/phase shifting parts of a same width and at a pitch of several µm to several ten µm, the ratio (aspect ratio=thickness/width) of thickness to width of the gold part is as high as 5 or more. It is not easy to manufacture a structure having such a high aspect ratio. For instance, patent literature 1 and patent literature 2 are proposed as methods for manufacturing a diffraction grating provided with a structure of such a high aspect ratio.

The diffraction grating manufacturing method disclosed in patent literature 1 is a method for manufacturing a diffraction grating for use in an X-ray Talbot interferometer, and has the following steps. At first, a metal sheet layer is formed on one surface of a glass substrate. Then, patterning is performed by coating an ultraviolet photosensitive resin on the metal sheet layer, and subjecting the ultraviolet photosensitive resin to pattern exposure with use of an optical lithography mask for a phase-type diffraction grating followed by development. Then, an X-ray absorbing metal part is formed on a portion of the metal sheet layer where the ultraviolet photosensitive resin is removed, by a metal plating method. Then, the patterned ultraviolet photosensitive resin, and a portion of the metal sheet layer corresponding to the patterned ultraviolet photosensitive resin are removed. By performing the above operation, a phase-type diffraction grating is manufactured. Then, patterning is performed by coating an ultraviolet photosensitive resin on a surface of the phase-type diffraction grating corresponding to the one surface of the glass substrate, and by subjecting the ultraviolet photosensitive resin to pattern exposure from the other surface of the phase-type diffraction grating with use of the phase-type diffraction grating as an optical lithography mask followed by development. Then, applying a voltage via the metal sheet layer by a metal plating method forms an X-ray absorbing metal part on the X-ray absorption part of the phase-type diffraction grating, on a portion where the ultraviolet photosensitive resin is removed. Thereafter, the aforementioned steps are repeated until the X-ray absorbing metal part has a required thickness, with use of a phase-type diffraction grating having the newly formed X-ray absorbing metal part, as a new optical lithography mask. Thus, an amplitude-type diffraction grating is manufactured.

Further, the method for manufacturing a diffraction grating for an X-ray Talbot interferometer disclosed in patent literature 2 has the following steps:

a groove forming step of forming a groove by alternately repeating an etching step of forming a concave portion by performing preferential reactive ion etching to a silicon substrate with use of gas containing F atoms in an inductively coupled plasma processing apparatus, and a protective film deposition step of depositing a polymer film, as a protective film, on a bottom surface and side wall surfaces of the concave portion by introducing fluorocarbon-based gas in the inductively coupled plasma processing apparatus;

a silicon oxide film forming step of forming an electrically insulating film constituted of a silicon oxide film on a bottom surface and side wall surfaces of the groove by introducing oxygen gas in the inductively coupled plasma processing apparatus;

a silicon exposing step of removing a portion of the electrically insulating film on the bottom surface of the groove, and exposing a silicon portion of the silicon substrate on the bottom surface by performing reactive ion etching with use of gas containing F atoms in the inductively coupled plasma processing apparatus; and an electroplating step of subjecting the exposed surface of the silicon portion as a seed layer to electroplating to precipitate an X-ray absorbing metal part in the groove.

In the diffracting grating manufacturing method disclosed in patent literature 1, the aforementioned steps are repeated until the X-ray absorbing metal part has a required thickness. This requires a certain time and involves a cumbersome operation.

In the method for manufacturing an X-ray Talbot diffraction grating disclosed in patent literature 2, however, is relatively simple, because the aforementioned steps are not repeated.

However, in the case where an electrically insulating film constituted of a silicon oxide film to be formed on a bottom surface and side wall surfaces of the groove in the silicon oxide film forming step in patent literature 2 is formed by introducing oxygen in an inductively coupled plasma processing apparatus, the thickness of the electrically insulating film is at most about 2 nm, referring to a non-patent literature cited in patent literature 2 i.e. "development of new deep RIE technology using dual side wall protective film" by Junji Ohara and other five persons, Denso Technical Review issued by Denso Corporation in the year of 2000, pp. 45-50, Vol. 5, No. 1, 2000". It seems to be difficult to further increase the thickness of the film, even if a discharge condition relating to plasma processing, or parameters such as a flow rate of oxygen or a time for irradiating oxygen is changed. Although the aforementioned film may function as a mask for reactive ion etching in the silicon exposing step in patent literature 2, the film has such a small thickness as described above, and does not have a sufficient fineness for actual use. Accordingly, the aforementioned film may not sufficiently function as the electrically insulating film in the electroplating step in patent literature 2, and does not function as an appropriate film in the electroplating step. Since the entirety of a silicon substrate is electrically conductive, X-ray absorbing metal may also grow on the side wall surfaces of the groove in the electroplating step. As a result, hollow portions (voids i.e. portions in which metal is not filled) may be generated in the X-ray absorbing metal part. It is technically difficult to finely fill the groove with the X-ray absorbing metal by electroplating.

CITATION LIST

Patent Literature

Patent literature 1: JP 2009-037023A
Patent literature 2: JP2010-185728A

SUMMARY OF INVENTION

In view of the above, an object of the present invention is to provide a method for manufacturing a metal grating structure capable of finely forming metal parts of a grating structure by an electroforming method, with use of a silicon substrate. Another object of the present invention is to provide a metal grating structure manufactured by the metal grating structure manufacturing method, and an X-ray imaging device incorporated with the metal grating structure.

In the metal grating structure manufacturing method of the present invention, in filling a concave portion formed in a silicon substrate with metal by an electroforming method, an insulating layer is formed in advance on an inner surface of the concave portion by a thermal oxidation method. Accordingly, the metal grating structure manufacturing method is advantageous in finely forming metal parts of the grating structure. A metal grating structure of the present invention is manufactured by the above manufacturing method, and an X-ray imaging device of the present invention is incorporated with the metal grating structure.

These and other objects, features and advantages of the present invention will become more apparent upon reading the following detailed description along with the accompanying drawings.

BRIEF DESCRIPTION OF DRAWINGS

FIG. 1 is a perspective view showing a configuration of a metal grating structure according to an embodiment;

DESCRIPTION OF EMBODIMENTS

Figure 2A:
FIGS. 2A through 2C are diagrams (part 1) for describing a method for manufacturing a metal grating structure according to an embodiment.

In the following, an embodiment of the present invention is described referring to the accompanying drawings. Constructions identified by the same reference numerals in the drawings are the same constructions and not repeatedly described unless necessary. Further, in the specification, in the case where the elements are generically referred to, the elements are indicated with reference numerals without suffixes, and in the case where the elements are individually referred to, the elements are indicated with reference numerals with suffixes.

(Metal Grating Structure)

FIG. 1 is a perspective view showing a configuration of a metal grating structure according to an embodiment. As shown in FIG. 1, a metal grating structure DG according to the embodiment is provided with a first silicon part 11, and a grating part 12 formed on the first silicon part 11. As shown in FIG. 1, the first silicon part 11 has a plate form or a layer form extending along the DxDy plane, in the case where a DxDyDz orthogonal coordinate system is defined. The grating part 12 has a predetermined thickness H (a length in the Dz direction perpendicular to the grating plane DxDy (a direction normal to the grating plane DxDy)). The grating part 12 is provided with plural second silicon parts 12a each linearly extending in one direction Dx, and plural metal parts 12b each having the predetermined thickness H and linearly extending in the one direction Dx. The second silicon parts 12a and the metal parts 12b are alternately disposed in parallel to each other. Accordingly, the metal parts 12b are disposed away from each other at a predetermined interval in a direction Dy orthogonal to the one direction Dx. In other words, the second silicon layers 12a are disposed away from each other at a predetermined interval in the direction Dy orthogonal to the one direction Dx. The predetermined interval (pitch) P is made constant in the embodiment. Specifically, the metal parts 12b (the second silicon parts 12a) are disposed at the same interval P in the direction Dy orthogonal to the one direction Dx. Each of the second silicon parts 12a has a plate form or a layer form extending along the DxDz plane orthogonal to the DxDy plane, and each of the metal parts 12b has a plate form or a layer form extending along the DxDz plane.

Further, plural first insulating layers 12c are formed between the respective second silicon parts 12a and the respective metal parts 12b. Specifically, a first insulating layer 12c is formed on both side surfaces of each of the second silicon parts 12a. In other words, the first insulating layer 12c is formed on both side surfaces of each of the metal parts 12b. The first insulating layer 12c is an oxide silicon layer (an $SiO_2$ film or a silicon oxide film) which functions as an element for electrically insulating between the respective second silicon layer 12a and the respective metal part 12b.

Further, second insulating layers 12d are formed on upper surfaces (apex portions) of the respective second silicon parts 12a. The second insulating layer 12d functions as an element for electrically insulating the second silicon layer 12a by an electroforming method described later, and is made of an oxide film, for instance. Examples of the oxide film are a silicon oxide film (an $SiO_2$ film or a silicon oxide film), and an alumina film (an $Al_2O_3$ film or an aluminum oxide film).

The first silicon part 11, the second silicon parts 12a, the first insulating layers 12c, and the second insulating layers 12d function to transmit X-ray, and the metal parts 12b function to absorb X-ray. Accordingly, the metal grating structure DG according to one aspect functions as a diffraction grating by appropriately setting the predetermined interval P according to the wavelength of X-ray. A metal composing the metal part 12b is preferentially selected from the metals absorbing X-ray. Examples of the metal include metal elements or precious metal elements having a relatively heavy atomic weight, specifically, gold (Au), platinum (Pt), rhodium (Rh), ruthenium (Ru), and iridium (Ir). Further, the metal part 12b has an appropriate thickness H so as to sufficiently absorb X-ray according to the device specifications, for instance. In view of the above, the ratio (aspect ratio=thickness/width) of thickness H to width W of the metal part 12b is set to an aspect ratio as high as 5 or more. The width W of the metal part 12b corresponds to the length of the metal part 12b in the direction (width direction) Dy orthogonal to the one direction (longitudinal direction) Dx, and the thickness H of the metal part 12b corresponds to the length of the metal part 12b in the direction (depth direction) Dz normal to the plane DxDy defined by the one direction Dx and the direction Dy orthogonal to the one direction Dx.

The metal grating structure DG provided with the metal parts 12b having such a high aspect ratio is manufactured by a resist layer forming step of forming a resist layer on a principal plane of a silicon substrate; a patterning step of patterning the resist layer to remove the patterned portion of the resist layer; an etching step of etching the silicon substrate at a portion where the resist layer is removed by a dry etching method to form a concave portion of a predetermined depth; an insulating layer forming step of forming an insulating layer on an inner surface of the concave portion in the silicon substrate by a thermal oxidation method; a removing step of removing a portion of the insulating layer formed on a bottom portion of the concave portion; and an electroforming step of applying a voltage to the silicon substrate to fill the concave portion with metal by an electroforming method. For instance, the concave portion is a slit groove in the case of a one-dimensional grating structure, and is a columnar hole (columnar pore) in the case of a two-dimensional grating structure. In the following, a method for manufacturing the metal grating structure DG in which the concave portion is a slit groove is described in detail. The same description is applied to a configuration, in which a concave portion has another shape such as a columnar hole.

(Manufacturing Method)

Figure 5:
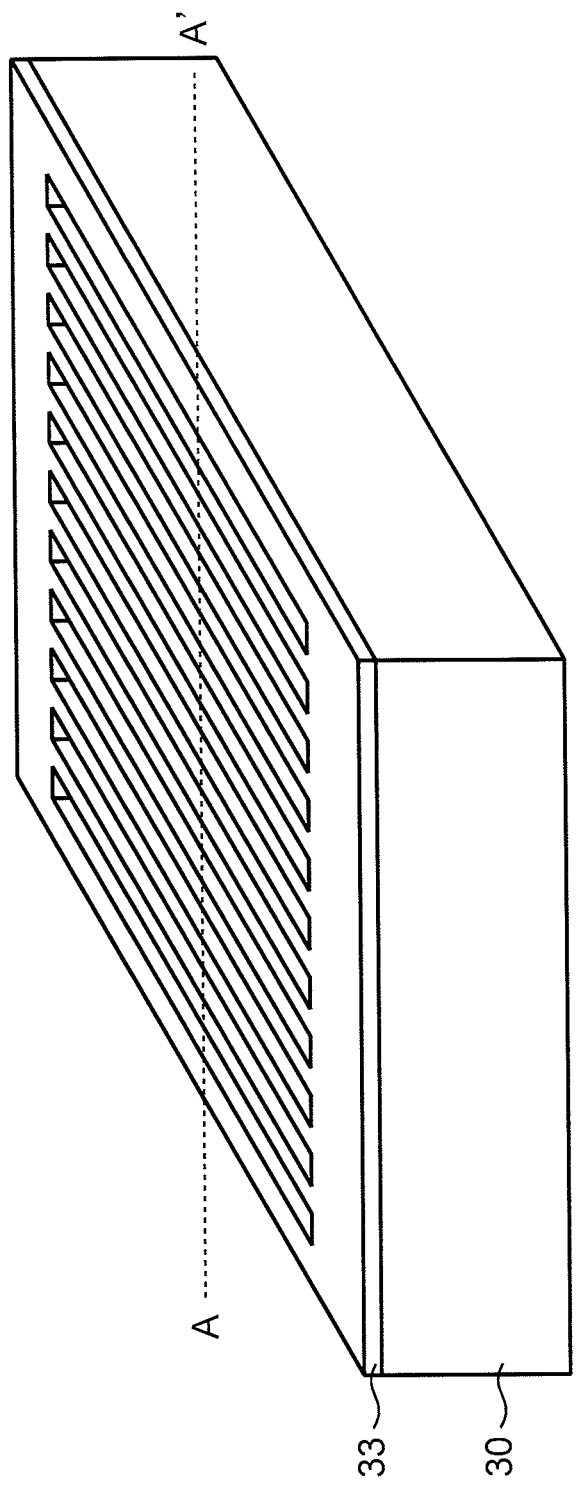
FIG. 5 is a perspective view showing a silicon substrate during a process of manufacturing a metal grating structure according to the embodiment.
Figure 6B:
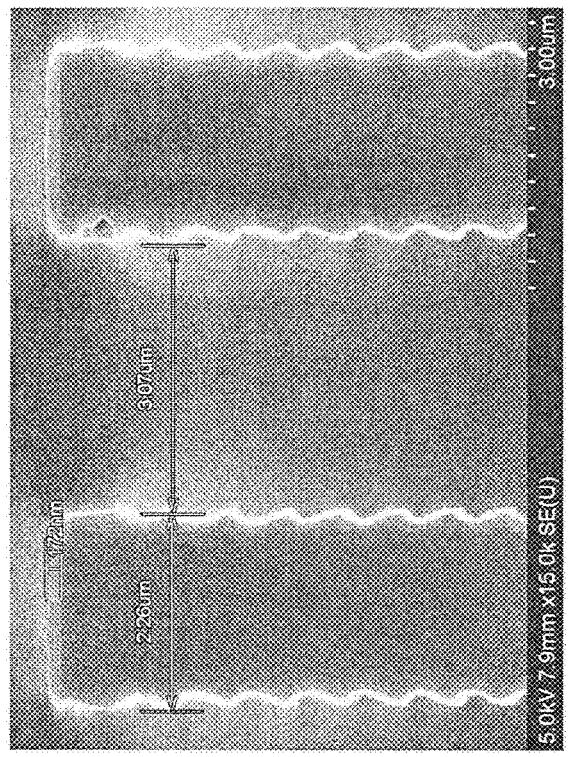
FIGS. 6A and 6B are diagrams showing a state of a silicon substrate which has undergone ICP dry etching by a Bosch process.
Figure 6A:
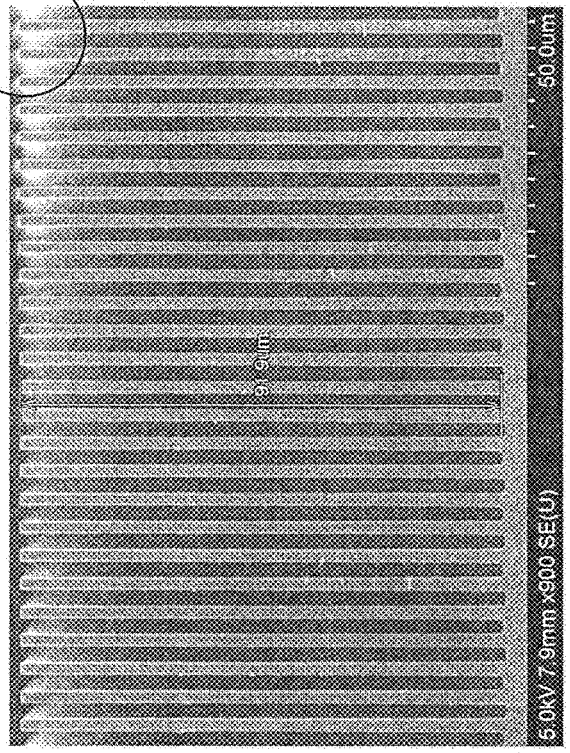

FIGS. 2A through 4C are diagrams for describing a method for manufacturing a metal grating structure according to an embodiment. FIG. 5 is a perspective view showing a silicon substrate during a process of manufacturing the metal grating structure according to the embodiment. FIGS. 6A and 6B are diagrams showing a state of a silicon substrate which has undergone ICP dry etching by a Bosch process. FIG. 6B is a partially enlarged view of FIG. 6A.

At first, a silicon substrate 30 is prepared for manufacturing a metal grating structure DG according to the embodiment (see FIG. 2A). Preferably, the silicon substrate 30 is an n-type silicon substrate, in which most of the carriers are electrons.

The n-type silicon substrate is rich in conductive electrons. Accordingly, connecting the silicon substrate to the negative pole of a power source and applying a negative potential to the silicon substrate for obtaining cathode polarization causes a so-called ohmic contact with a plating solution 46 in an electroforming step described later. This allows a current to flow and makes it easy to cause a reduction reaction, thereby making it easy to precipitate metal.

Then, a resist layer 33 is formed on the principal plane of the silicon substrate 30 (resist layer forming step). The resist layer 33 is patterned, and the patterned portion of the resist layer 33 is removed (patterning step, see FIGS. 2B, 2C, 3A, and 3B). The resist layer is a layer which functions as a protective film against etching in performing the etching.

For instance, the resist layer 33 may be made of a same material as an insulating layer 34 described later. For instance, the resist layer 33 may be a silicon oxide film 33a having an insulating property and resistant against an etching process in an etching step that follows next. The silicon oxide film 33a is used as a patterned resist layer 33, and a photosensitive resin layer (photoresist film) is used for patterning the silicon oxide film 33a. The term "resistant" does not necessarily mean that a target portion is not etched at all, but a target portion is less likely to be etched in an etching process. This means that during etching of a portion to be etched, the resist layer acts as a protective layer which protects a portion that should not be etched. In the case where the resist layer 33 and the insulating layer 34 are made of a same material as described above, the resist layer 33 (in this example, the silicon oxide film 33a) is formed to have a film thickness t1 larger than a film thickness t2 of the insulating layer 34 so that the resist layer 33 remains after an etching step that follows next, and after a removing step described later.

Further, for instance, the resist layer 33 may be made of a material different from the material of the insulating layer 34. For instance, the resist layer 33 may be a metal oxide film 33b having an insulating property and resistant not only against an etching process in an etching step but also against a removing process in a removing step. An example of the metal oxide film 33b is an alumina film ($Al_2O_3$ film). The metal oxide film 33b is used as a patterned resist layer 33. A photosensitive resin layer (photoresist film) is used for patterning the metal oxide film 33b. In the above configuration, the metal oxide film 33b itself is resistant against an etching process in an etching step and a removing process in a removing step. Accordingly, it is not necessary to set the film thickness t1 of the resist layer 33 larger than the film thickness t2 of the insulating layer 34, and the film thickness t1 may be any value, as far as the metal oxide film 33b has an electrically insulating property in an electroforming method.

The thus-configured silicon oxide film 33a and the thus-configured metal oxide film 33b serve as layers having an insulating property, and capable of remaining after an etching step and a removing step.

Further, for instance, the resist layer 33 may be made of a material different from the material of the insulating layer 34. For instance, the resist layer 33 may be a metal film 33c resistant against an etching process in an etching step and oxidizable. An example of the metal film 33c is an aluminum film (Al film). The metal film 33c is used as a patterned resist layer 33. A photosensitive resin layer (photoresist film) is used for patterning the metal film 33c. In the above configuration, a metal oxide film, preferably, an immobilized film resistant against corrosion in removing an oxide film 34 formed on a bottom surface BT of the structure, is formed on the top surface of the metal film 33c by thermal oxidation in an insulating film forming step described later, and resistance against a removing process in a removing step is acquired. Accordingly, it is not necessary to set the film thickness t1 of the resist layer 33 larger than the film thickness t2 of the insulating layer 34, and the film thickness t1 may be any value, as far as the metal film 33c has an electrically insulating property in an electroforming method. In the above configuration, the metal film 33c may be such that a metal part thereof remains in the inside of the metal oxide film, or the entirety of the metal film 33c may serve as a metal oxide film.

The oxidizable metal film 33c becomes a layer having an insulating property by thermal oxidation in the insulating layer forming step, and capable of remaining after an etching step and a removing step.

More specifically, in the case where the resist layer 33 is the silicon oxide film 33a, the silicon oxide film 33a is formed on the surface of the silicon substrate 30 as the resist layer 33. The silicon oxide film 33a is formed to have the thickness t1 thereof larger than the thickness t2 of the silicon oxide film 34 as the insulating layer 34 described later. The silicon oxide film 33a is formed by any of the well-known means i.e. a thermal oxidation method, a chemical vapor deposition method, an anode oxidation method, or a sputtering method. For instance, in the thermal oxidation method, an oxygen atmosphere (which may contain inert gas) or water vapor is introduced to a quartz tube in which the silicon substrate 30 is disposed, and the silicon substrate 30 is heated to a high temperature by heating the quartz tube by a heater in the oxygen atmosphere or in a gaseous atmosphere of the water vapor, whereby the silicon oxide film 33a of a predetermined thickness is formed on the surface of the silicon substrate 30. For instance, heating the silicon substrate 30 in an atmosphere of water vapor to be introduced by one liter/min at 1,150° C. for twenty minutes forms a silicon oxide film 33a of about 200 nm in thickness. Further, for instance, in the chemical vapor deposition (CVD) method, tetraethoxysilane (TEOS) as a kind of organic silanes is warmed, TEOS gas is generated by bubbling with use of carrier gas, and then, oxidation gas such as oxygen or ozone, and diluent gas such as helium gas are mixed with the TEOS gas, whereby raw material gas is generated. The thus generated raw material gas is introduced to a CVD apparatus such as a plasma CVD apparatus or an ozone CVD apparatus at a fixed temperature, whereby a silicon oxide film 33a of a predetermined thickness (for instance 200 nm in thickness) is formed on the surface of the silicon substrate 30 in the CVD apparatus. Further, for instance, in the anode oxidization method, the positive pole of a power source is connected to the silicon substrate 30, and a cathode electrode connected to the negative pole of the power source and the silicon substrate 30 are immersed in an electrolytic solution. Then, supplying a current to the silicon substrate 30 forms a silicon oxide film 33a of a predetermined thickness (for instance 200 nm in thickness) on the surface of the silicon substrate 30. The electrolytic solution is preferably an acidic solution which has a high acidity but does not dissolve an oxide film generated by anode oxidization, for instance, a solution of nitric acid, hydrochloric acid, sulfuric acid, oxalic acid, or phosphoric acid. The cathode electrode is preferably made of a metal that does not dissolve in the electrolytic solution, for instance, gold (Au) or platinum (Pt). The silicon oxide film 33a is formed at least on the upper surface of the silicon substrate 30, but may be formed on the back surface or on a side surface of the silicon substrate 30. Use of the silicon oxide film 33a as the resist layer 33 as described above makes it possible to use one of the well-known means i.e. the thermal oxidation method, the chemical vapor deposition method, the anode oxidation method, or the sputtering method. This is advantageous in relatively easily forming the silicon oxide film 33a.

Figure 2B:
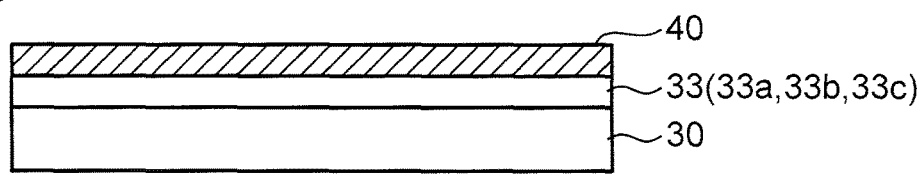
Figure 2C:
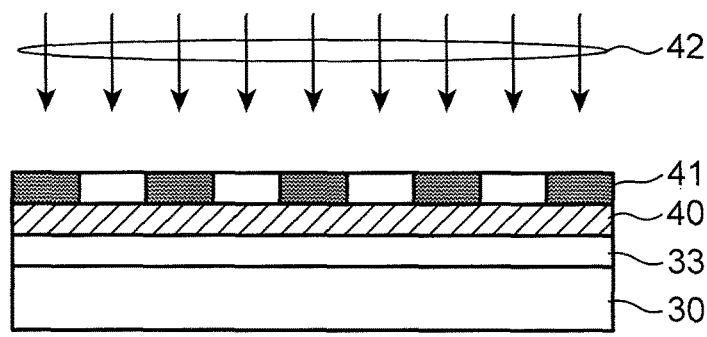

Subsequently, a photosensitive resin layer 40 is formed on the silicon oxide film 33a formed on the silicon substrate 30 by spin coating, for instance (see FIG. 2B). The photosensitive resin layer 40 is made of a material used in lithography, and having a physical property such that the solubility thereof changes by light (not only including visible light but also including ultraviolet light) or an electron beam. The present embodiment is not limited to the above. For instance, a resist layer for electron beam exposure may be formed, in place of the photosensitive resin layer 40. Subsequently, as a photolithography step, the photosensitive resin layer 40 is patterned by a lithography method (see FIG. 2C), and the patterned portion of the photosensitive resin layer 40 is removed (see FIG. 3A). More specifically, a lithography mask 41 is pressed against the photosensitive resin layer 40, ultraviolet light 42 is irradiated onto the photosensitive resin layer 40 via the lithography mask 41, and the photosensitive resin layer 40 is subjected to pattern exposure followed by development (see FIG. 2C). Then, the unexposed portion (or the exposed portion) of the photosensitive resin layer 40 is removed (see FIG. 3A).

Figure 3A:
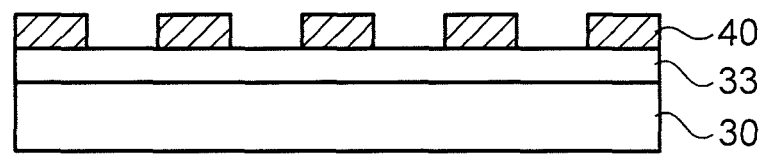
FIGS. 3A through 3C are diagrams (part 2) for describing the metal grating structure manufacturing method according to the embodiment.
Figure 3B:
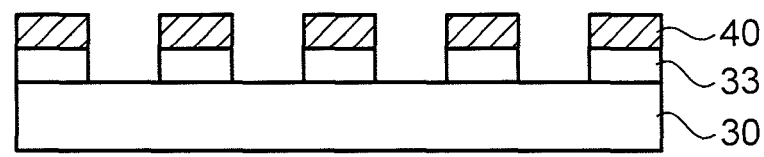

Subsequently, the silicon oxide film 33a is patterned by removing a portion of the silicon oxide film 33a where the photosensitive resin layer 40 is removed by etching, with use of the patterned photosensitive resin layer 40 as a mask (see FIG. 3B). More specifically, for instance, the silicon oxide film 33a is patterned by reactive etching (RIE) with use of $CHF_3$ gas. Further, for instance, the silicon oxide film 33a may be patterned by wet etching with use of hydrofluoric acid. The etching of the silicon oxide film 33a as the resist layer 33 in the patterning step may be performed by another etching method.

In the case where the metal oxide film 33b is used in place of the silicon oxide film 33a as the resist layer 33 in forming the silicon oxide film 33a as described above, the metal oxide film 33b is formed by a film forming method such as a chemical vapor deposition method or a sputtering method, for instance. Further, RIE with use of appropriate reactive gas is used in patterning the metal oxide film 33b in the patterning step. For instance, in the case where the metal oxide film 33b is an alumina film 33b, the alumina film 33b of about 150 nm in thickness is formed by a sputtering method, and then, the alumina film 33b is patterned by RIE with use of chlorine gas.

Further, in the case where a metal film 33c is used in place of the silicon oxide film 33a as the resist layer 33 in forming the silicon oxide film 33a as described above, the metal film 33c is formed by a film forming method such as a vacuum deposition method or a sputtering method. Further, RIE with use of appropriate reactive gas is used in patterning the metal film 33c in the patterning step. For instance, in the case where the metal film 33c is an aluminum film 33c, the aluminum film 33c of about 150 nm in thickness is formed by a sputtering method, and the aluminum film 33c is patterned by RIE with use of chlorine gas.

Figure 3C:
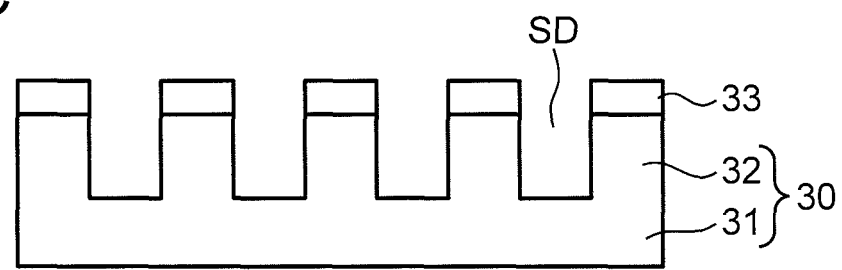

Then, the portion of the silicon substrate 30 where the photosensitive resin layer 40 and the resist layer 33 are removed by a dry etching method are etched to a predetermined depth H in the normal direction Dz. By performing the above operation, a slit groove SD is formed (see FIG. 3C, etching step). FIG. 5 shows a structure example of the silicon substrate 30 after the etching step. FIG. 3C shows a cross section of the silicon substrate 30 taken along the line A-A' in FIG. 5.

More specifically, the silicon substrate 30 is etched by ICP (Inductively Coupled Plasma) dry etching to the predetermined depth H from the surface of the silicon substrate 30, with use of the patterned photosensitive resin layer 40 and the patterned resist layer 33 as masks. By the ICP dry etching, the photosensitive resin layer 40 is removed. The resist layer 33 may be slightly etched.

In the foregoing example, in the case where the resist layer 33 is the silicon oxide film 33a, the thickness of the silicon oxide film 33a decreases from about 200 nm to about 170 nm by ICP dry etching. Further, in the case where the resist layer 33 is the alumina film 33b as the metal oxide film 33b, the thickness of the alumina film 33b decreases from about 150 nm to about 130 nm, for instance. Further, in the case where the resist layer 33 is the aluminum film 33c as the metal film 33c, the thickness of the aluminum film 33c decreases from about 150 nm to about 130 nm by ICP dry etching, for instance.

The ICP dry etching makes it possible to perform vertical etching with a high aspect ratio. Accordingly, the ICP dry etching is preferably an ASE process by an ICP apparatus. The ASE (Advanced Silicon Etch) process is a process including a step of etching a silicon substrate by RIE (reactive ion etching) with use of F radicals and F ions in $SF_6$ plasma, and a step of depositing a polymer film having a composition analogous to Teflon (registered trademark) on a wall surface by polymerization reaction of $CF_X$ radicals and ions thereof in $C_4F_8$ plasma for functioning the polymer film as a protective film, wherein the above steps are repeatedly performed. Further, ICP dry etching is advantageous in performing vertical etching with a high aspect ratio. Accordingly, it is more preferable to alternately perform side wall protection and bottom surface etching by alternately repeating a state enriched with $SF_6$ plasma and a state enriched with $C_4F_8$ plasma, like a Bosch process. FIGS. 6A and 6B show a state of a silicon substrate 30 etched by a Bosch process as described above. The dry etching method is not limited to the ICP dry etching, but any other technique may be applied. For instance, an etching technology such as parallel plate type reactive ion etching (RIE), dry etching with magnetic neutral line plasma (NLD), chemically assisted ion beam (CAIB) etching, or electron cyclotron resonance reactive ion beam (ECRIB) etching may be applied.

A plate like portion (a layer portion or a wall portion) 32 of the silicon substrate 30 that remains along the DxDz plane after the etching serves as a second silicon part 12a, and a plate like portion (a base portion) 31 of the silicon substrate 30 that remains along the DxDy plane after the etching serves as a first silicon part 11.

Subsequently, an insulating layer 34 of a predetermined thickness is formed over the entirety of the inner surface of the slit groove SD in the silicon substrate 30 by a thermal oxidation method to have an insulating property in an electroforming method in an electroforming step described later (see FIG. 4A, insulating layer forming step). The insulating layer 34 is a silicon oxide film 34a because the silicon substrate 30 is used. The silicon oxide film 34a as the insulating layer 34 is formed to have a thickness of about 40 nm, for instance. The silicon oxide film 34a is formed at least on the inner surface of the slit groove SD in the silicon substrate 30, but may also be formed on the back surface or on a side surface of the silicon substrate 30. The thermal oxidation method is such that an oxide film is grown to form on a surface of a target material to be oxidized (in this embodiment, the inner surface of a concave portion of the silicon substrate 30) by heating the target material in a gaseous atmosphere of oxygen or water vapor. Accordingly, it is possible to obtain a very fine oxide film having a desired adhesiveness to the material. Further, the thermal oxidation method is advantageous in precisely controlling the film thickness by adjusting the flow rate of gaseous atmosphere or the heating time of gaseous atmosphere. This makes it easy to obtain oxide films in a film thickness range from a film thickness of several nm to a film thickness of micron order. Accordingly, the thermal oxidation method is appropriate as a method for forming the insulating layer 34 in an electroforming method in an electroforming step.

More specifically, in the case where the resist layer 33 is the silicon oxide film 33a, for instance, a silicon oxide film 33a of a substantially uniform thickness was formed over the entirety of the inner surface of a slit groove of about 40 nm in depth by heating the silicon substrate 30 in an atmosphere of oxygen to be introduced at a flow rate of 200 ml/min at 1,000° C. for sixty minutes. Further, for instance, a silicon oxide film 33a of a substantially uniform thickness was formed over the entirety of the inner surface of a slit groove of about 40 nm in depth by heating the silicon substrate 30 in an atmosphere of water vapor to be introduced at a flow rate of 1 liter/min at 1,150° C. for four minutes.

Further, in the case where the resist layer 33 is the metal oxide film 33b (in this example, the alumina film 33b), a silicon oxide film 33a of a substantially uniform thickness was formed over the entirety of the inner surface of a slit groove of about 40 nm in depth by heating the silicon substrate 30 in an atmosphere of water vapor to be introduced at a flow rate of 1 liter/min at 1,150° C. for four minutes.

Further, in the case where the resist layer 33 is the metal film 33c (in this example, the aluminum film 33c), a silicon oxide film 33a of a substantially uniform thickness was formed over the entirety of the inner surface of a slit groove of about 40 nm in depth by heating the silicon substrate 30 in an atmosphere of oxygen to be introduced at a flow rate of 200 ml/min at 1,000° C. for sixty minutes.

In the case where the resist layer 33 is the silicon oxide film 33a or the metal oxide film 33b, an oxide film is hardly formed on the surface of the resist layer 33 by thermal oxidation in the insulating layer forming step. In the foregoing example, in the case where the resist layer 33 is the silicon oxide film 33a, the thickness of the silicon oxide film 33a changed from about 170 nm to about 180 nm by thermal oxidation in the insulating layer forming step. In the case where the resist layer 33 is the alumina film 33b, the thickness of the alumina film 33b changed from about 130 nm to about 140 nm by thermal oxidation in the insulating layer forming step.

Figure 4A:
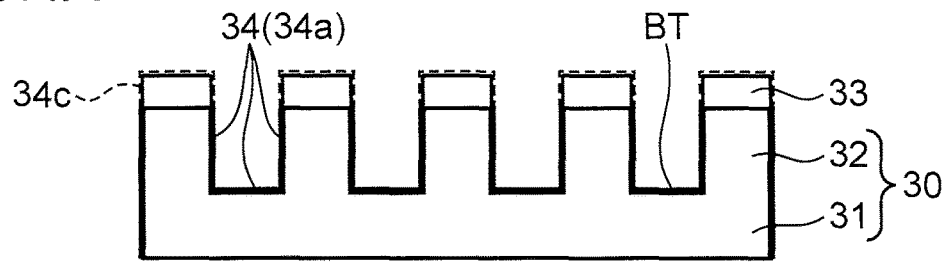
FIGS. 4A through 4C are diagrams (part 3) for describing the metal grating structure manufacturing method according to the embodiment.
Figure 4B:
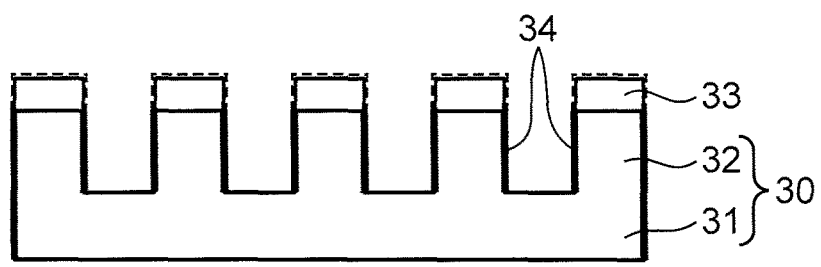
Figure 4C:
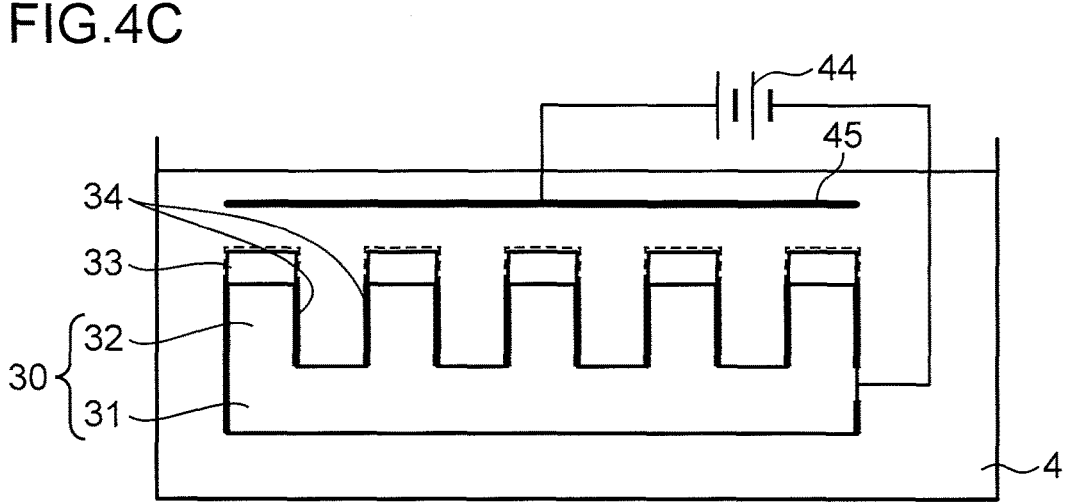

On the other hand, in the case where the resist layer 33 is the metal film 33c, as shown by the broken line in FIGS. 4A through 4C, a metal oxide film 34c is formed on the surface of the metal film 33c by thermal oxidation in the insulating layer forming step. Thus, the metal film 33c as the resist layer 33 acquires resistance against a removing process in a removing step, and acquires an insulating property in an electroforming method in an electroforming step. In the case where the metal film 33c is an aluminum film, an alumina film as an immobilized film is formed. In the foregoing example, an alumina film 34c of about 80 nm in thickness was formed.

Subsequently, a portion of the insulating layer 34 formed on the bottom portion BT of the slit groove SD is removed (removing step, see FIG. 4B). More specifically, a portion of the insulating layer 34 formed on the bottom portion BT of the slit groove SD is removed by ICP dry etching of a dry etching method.

The ICP dry etching has high vertical directionality. Accordingly, the insulating layer 34 formed on the inner side surfaces of the slit groove SD (the insulating layer 34 formed on both wall surfaces (both side surfaces) of the plate like portion 32 of the silicon substrate 30) has a sufficient thickness capable of functioning as an insulating layer at the point of time when the portion of the insulating layer 34 formed on the bottom portion BT of the slit groove SD is removed. The insulating layer 34 formed on the inner side surfaces of the slit grove SD may have such a thickness as to exhibit a function of cutting off a voltage to be applied to the plate like portion 32 of the silicon substrate 30 (a function of electrically insulating the plate like portion 32) in the electroforming step that follows next, for instance, may have a thickness of about 10 nm or more by cooperation with the resist layer 33 having an insulating property (the silicon oxide film 33a, the metal oxide film 33b, or a metal oxide film formed on the top surface of the metal film 33c). The insulating layers 34 formed on the inner side surfaces of each of the slit grooves SD (the insulating layers 34 formed on both wall surfaces (both side surfaces) of each of the plate like portions 32 of the silicon substrate 30) serve as first insulating layers 12c formed between the respective second silicon parts 12a and the respective metal parts 12b.

In the case where the resist layer 33 is the silicon oxide film 33a, the silicon oxide film 33a as the resist layer 33 is also etched on the plate like portion 32 of the silicon substrate corresponding to the second silicon part 12a, by ICP dry etching with use of $CHF_3$ gas. However, the thickness t1 of the silicon oxide film 33a after the patterning is larger than the thickness t2 of the silicon oxide film 34a as the insulating layer 34 (t1>t2). Accordingly, the silicon oxide film 33a as the resist layer 33 remains at the point of time when the portion of the silicon oxide film 34a as the insulating layer 34 formed on the bottom portion BT of the slit groove SD is removed. For instance, in the foregoing example, the silicon oxide film 33a remains, although the thickness thereof decreases from 180 nm to 100 nm.

Further, in the case where the resist layer 33 is the metal oxide film (for instance, an alumina film) 33b, the metal oxide film 33b as the resist layer 33 is hardly etched on the plate like portion 32 of the silicon substrate corresponding to the second silicon part 12a, by ICP dry etching with use of $CHF_3$ gas. For instance, in the foregoing example, the alumina film 33b of about 140 nm in thickness is hardly etched and remains, only with the thickness thereof decreasing to about 135 nm, even if the portion BT of the silicon oxide film 34a (insulating layer 34) of 40 nm in thickness that has been formed on the bottom portion of the slide groove SD is etched and removed by ICP plasma dry etching in the removing step.

Further, in the case where the resist layer 33 is the metal film (for instance, an aluminum film) 33c, a metal oxide film (in this example, an alumina film) is formed on the top surface of the metal film 33c by thermal oxidation in the insulating layer forming step. Accordingly, the metal film 33c as the resist layer 33 is hardly etched on the plate like portion 32 of the silicon substrate corresponding to the second silicon part 12a by the ICP dry etching, thanks to the metal oxide film. For instance, in the foregoing example, an alumina film formed on the aluminum film 33c is hardly etched and remains, only with about 5 nm etching by the ICP dry etching in the removing step.

The resist layers 33 on the respective upper surfaces (apex portions) of the second silicon parts 12a that remain after the removing step serve as the second insulating layers 12d.

Subsequently, the slit groove SD is filled with metal by applying a voltage to the silicon substrate 30 by an electroforming method (electroplating method) (electroforming step, see FIG. 4C). More specifically, the negative pole of a power source 44 is connected to the silicon substrate 30, and an anode electrode 45 connected to the positive pole of the power source 44 and the silicon substrate 30 are immersed in a plating solution 46. In the case where a silicon oxide film is formed on a portion of the silicon substrate 30 connected to the negative pole of the power source 44, the portion of the silicon substrate 30 is removed for electrical conduction between the negative pole of the power source 44 and the silicon substrate 30. By performing the above operation, metal is precipitated and grown on the bottom portion of the slit groove SD by electroforming from the silicon substrate 30 (plate like portion 31) side. Then, when the slit groove SD is filled with metal, the electroforming is ended. By performing the above operation, the metal grows by the same thickness H as the plate like portion 32 of the silicon substrate 30. In this way, the slit groove SD is filled with metal, and the metal part 12b is formed. The metal is preferentially selected from the elements capable of absorbing X ray, for instance, metal elements or precious metal elements having a relatively heavy atomic weight, specifically, gold (Au), platinum (Pt), rhodium (Rh), ruthenium (Ru), iridium (Ir), indium (In), and nickel (Ni).

The metal grating structure DG having the configuration as shown in FIG. 1 is manufactured by performing the above manufacturing steps.

The method for manufacturing a metal grating structure DG having the above configuration is capable of forming a slit groove SD of a high ratio of depth H to width W of the slit groove SD (the aspect ratio of the slit groove SD=depth H/width W), because a silicon substrate 30 is dry etched. Accordingly, the method for manufacturing a metal grating structure DG having the above configuration enables to manufacture a metal grating structure DG having a metal part 12b of a high aspect ratio by filling a slit groove SD of a high aspect ratio with metal. Then, in filling the slit groove SD with metal by an electroforming method in an electroforming step, at first, an insulating layer 34 is formed on the inner surface of the slit groove SD by a thermal oxidation method in an insulating layer forming step, and then, a portion of the insulating layer 34 formed on a bottom portion BT of the slit groove SD is removed in a removing step. Accordingly, in the insulating layer forming step, the insulating layer 34 is formed by the thermal oxidation method capable of forming a fine film having a high adhesiveness and capable of relatively easily controlling the film thickness. This is advantageous in forming a silicon oxide film ($SiO_2$ film) of a predetermined film thickness capable of securing electrical insulation by an electroforming method in an electroforming step, and is advantageous in insulating, by the insulating layer 34, a wall surface portion (a wall surface portion (inner side surface portions) of the slit groove SD) of a wall portion of the silicon substrate 30 (each of the plate like portions 32 of the silicon substrate 30) that constitutes the slit groove SD and that remains in the etching step, while making the bottom portion of the slit groove SD electrically conductive. Accordingly, the metal is securely precipitated and grown on the bottom portion of the slit groove SD, without precipitating and growing the metal on the wall surface (inner side surfaces) of the slit groove SD. Thus, the method for manufacturing a metal grating structure DG having the above configuration can effectively suppress generation of voids, because the metal is preferentially grown on the bottom portion of the slit groove SD. Accordingly, the method for manufacturing a metal grating structure DG having the above configuration is advantageous in finely forming the metal parts 12b of the grating structure by an electroforming method. In particular, a diffraction grating to be used in an X-ray Talbot interferometer and an X-ray Talbot-Lau interferometer requires a high aspect ratio in a metal part 12b. The method for manufacturing a metal grating structure DG according to this embodiment can secure such a high aspect ratio, for instance, an aspect ratio of 5 or more, preferably 10 or more, and more preferably 20 or more. In addition, the above method makes it possible to form a fine metal part 12b. Thus, the above method is suitable as a method for manufacturing a diffraction grating for use in an X-ray Talbot interferometer and an X-ray Talbot-Lau interferometer.

Further, in the method for manufacturing a metal grating structure DG according to this embodiment, the thickness of the resist layer 33 is formed to be larger than the thickness of the insulating layer 34 so that the resist layer 33 remains after the etching step and after the removing step, even in the case where the resist layer 33 and the insulating layer 34 are made of a same material, for instance, even in the case where the silicon oxide film 33a and the silicon oxide film 34a are formed. This allows the resist layer 33 to remain after the removing step, even if the resist layer 33 is etched and removed by the removing process in the removing step. Accordingly, in the method for manufacturing a metal grating structure DG having the above configuration, the apex portion (upper surface) of the wall portion of the silicon substrate 30 (each of the plate like portions 32 of the silicon substrate 30) that constitutes the slit groove SD and that remains in the etching step is also insulated by the electroforming method in the electroforming step. This is advantageous in securely obtaining an insulating property of the wall portion in the electroforming method by cooperation of the insulating layer 34 with the resist layer 33 that remains.

On the other hand, in the method for manufacturing a metal grating structure DG according to this embodiment, in the case where the resist layer 33 and the insulating layer 34 are made of materials different from each other, specifically, in the case where the resist layer 33 is made of a material having resistance against a removing process in a removing step and different from the material constituting the insulating layer 34, it is possible to preferentially remove only the insulating layer 34 in the removing step. After the removing step, the resist layer 33 remains. Forming the resist layer 33 and the insulating layer 34 of materials different from each other as described above makes it possible to form the resist layer 33 and the insulating layer 34 of materials different from each other in the etching rate, and makes it possible to preferentially remove only the portion BT of the insulating layer 34 formed on the bottom portion of the slit groove SD. For instance, the resist layer 33 is a metal oxide film 33b made of a material other than silicon, or is a metal film 33c made of a material other than oxidizable silicon, and the insulating layer 34 is a silicon oxide film. Accordingly, in the method for manufacturing a metal grating structure DG having the above configuration, the apex portion (upper surface) of the wall portion of the silicon substrate 30 (each of the plate like portions 32 of the silicon substrate 30) that constitutes the slit groove SD and that remains after the etching step is also insulated in the electroforming method in the electroforming step. This is advantageous in securely obtaining an insulating property of the wall portion in the electroforming method by cooperation of the insulating layer 34 with the resist layer 33 that remains.

In patent literature 2, the etching mask to be used in the etching step (groove forming step) is a photoresist mask (see the paragraph [0044] of patent literature 2). Accordingly, the photoresist mask that remains after the etching step on the apex portion (on one surface of the silicon substrate) of the wall portion of the silicon substrate (unetched portion of the silicon substrate) that constitutes the side wall surfaces of the groove, reacts with oxygen in the silicon oxide film forming step, and it is highly likely that the photoresist mask does not remain in the electroplating step. The entirety of the silicon substrate is electrically conductive. Accordingly, in the electroplating step, it is highly likely that X-ray absorbing metal grows on the apex portion of the wall portion of the silicon substrate, and as a result, a hollow portion (voids or portions in which metal is not filled) may be generated in the X-ray absorbing metal part. However, in the method for manufacturing a metal grating structure DG according to this embodiment, as described above, the resist layer 33 having an insulating property remains in performing the electroforming method in the electroforming step. Accordingly, the wall portion is securely insulated by cooperation of the insulating layer 34 with the resist layer 33 that remains. In this aspect also, the method for manufacturing a metal grating structure DG according to this embodiment is advantageous in finely forming the metal parts of a grating structure by an electroforming method in an electroforming step.

Further, the method for manufacturing a metal grating structure DG according to this embodiment employs RIE (Reactive Ion Etching) in the etching step. This enables to perform anisotropic etching. Accordingly, it is possible to etch the silicon substrate 30 along the depth direction (laminated direction) to thereby relatively easily form the slit groove SD.

Further, in the method for manufacturing a metal grating structure DG according to this embodiment, the silicon substrate 30 is dry etched by a Bosch process. This is advantageous in forming a side surface of the slit groove SD into a flat shape, thereby forming the metal grating structure DG with high precision. In particular, in the case where the metal grating structure DG functions as a diffraction grating, the incident surface or the exit surface is formed into a flat surface, which is preferable.

In the foregoing embodiment, the diffraction grating DG has a one-dimensional periodic structure. The present invention is not limited to the above. The diffraction grating may be a diffraction grating of a two-dimensional periodic structure. For instance, the diffraction grating DG of a two-dimensional periodic structure is configured such that grating dots serving as diffraction members are equidistantly arranged away from each other at a predetermined interval in linearly independent two directions. The diffraction grating of a two-dimensional periodic structure having the above configuration can be formed by forming holes of a high aspect ratio in a flat surface at a two-dimensional period, and filling the holes with metal as with the above case; or by forming upright columns of a high aspect ratio on a flat surface at a two-dimensional period, and filling a space around the columns with metal as with the above case.

(Talbot Interferometer and Talbot-Lau Interferometer)

The metal grating structure DG according to this embodiment is capable of forming metal parts with a high aspect ratio. Accordingly, the metal grating structure DG can be appropriately used in an X-ray Talbot interferometer and an X-ray Talbot-Lau interferometer. In the following, an X-ray Talbot interferometer and an X-ray Talbot-Lau interferometer incorporated with the metal grating structure DG are described.

Figure 7:
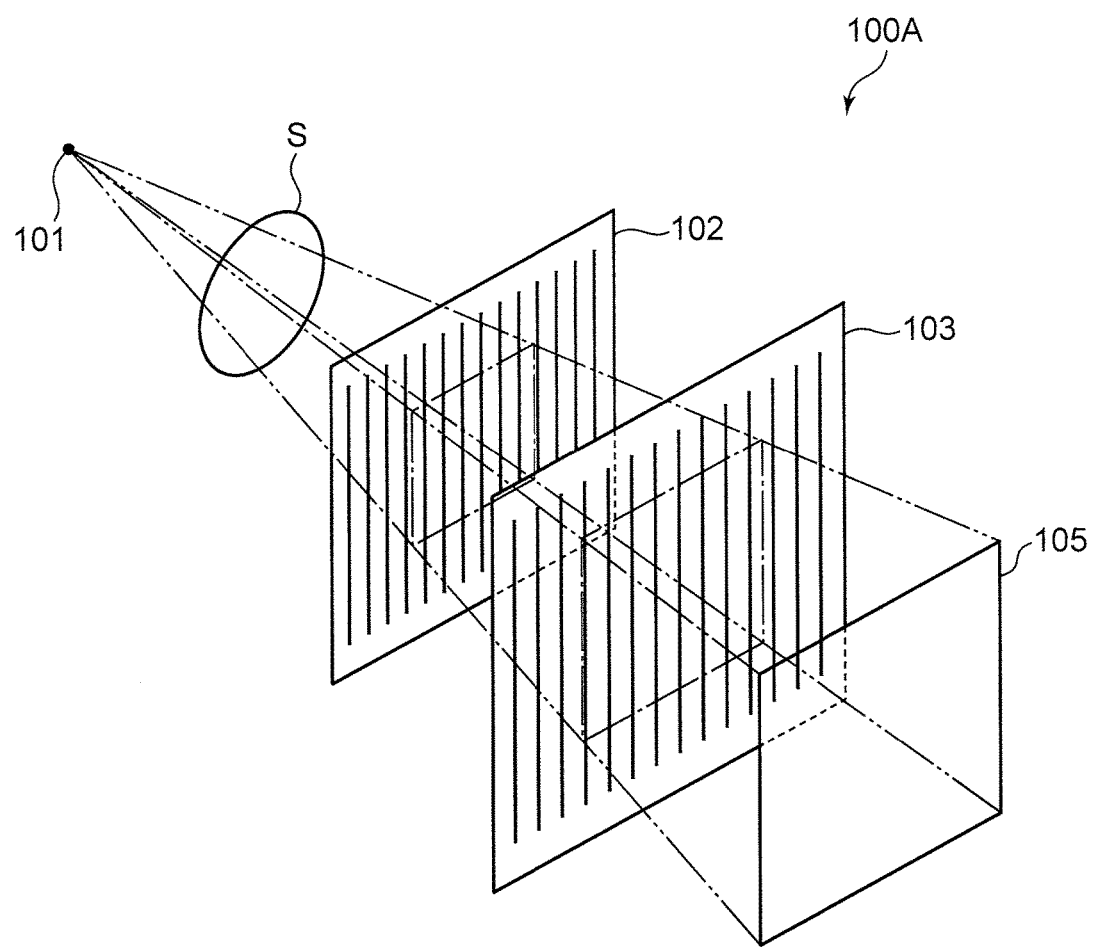
FIG. 7 is a perspective view showing a configuration of an X-ray Talbot interferometer according to an embodiment.
Figure 8:
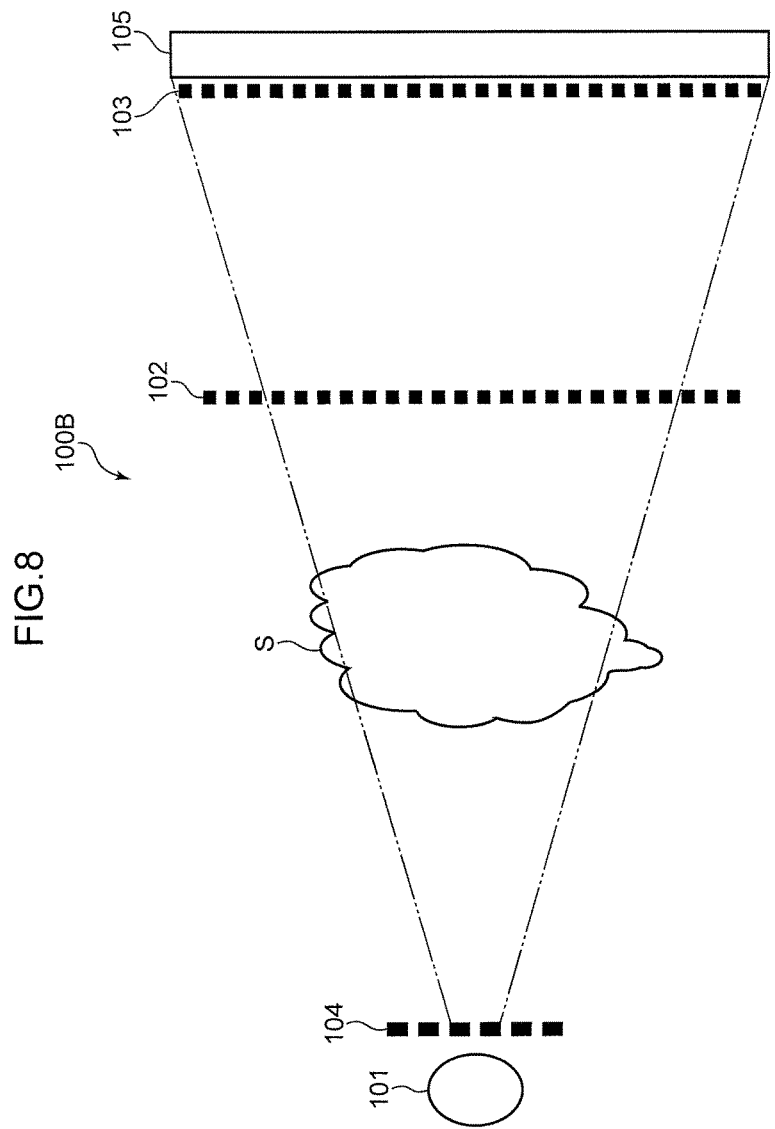
FIG. 8 is a top plan view showing a configuration of an X-ray Talbot-Lau interferometer according to an embodiment.

FIG. 7 is a perspective view showing a configuration of an X-ray Talbot interferometer according to an embodiment. FIG. 8 is a top plan view showing a configuration of an X-ray Talbot-Lau interferometer according to an embodiment.

As shown in FIG. 7, an X-ray Talbot interferometer 100A according to the embodiment is provided with an X-ray source 101 which outputs X-ray of a predetermined wavelength, a first diffraction grating 102 of phase-type which diffracts the X-ray output from the X-ray source 101, and a second diffraction grating 103 of amplitude-type which forms image contrast by diffracting the X-ray diffracted by the first diffraction grating 102. The first and second diffraction gratings 102 and 103 are configured to satisfy the conditions that define an X-ray Talbot interferometer. An X-ray image having image contrast to be generated by the second diffraction grating 103 is detected by an X-ray image detector 105 which detects X-ray, for instance. In the X-ray Talbot interferometer 100A, at least one of the first diffraction grating 102 and the second diffraction grating 103 has the aforementioned metal grating structure DG.

The conditions for defining the Talbot interferometer 100A are expressed by the following formulas 1 and 2. The formula 2 is made based on the premise that the first diffraction grating 102 is a phase-type diffraction grating.

$$l = \lambda(a/(L+Z1+Z2)) \qquad \text{formula (1)}$$

$$Z1 = (m+\tfrac{1}{2}) \times (d^2/\lambda) \qquad \text{formula (2)}$$

where $l$ denotes a coherence length, $\lambda$ denotes a wavelength of X-ray (ordinarily, a center wavelength), $a$ denotes an aperture diameter of the X-ray source 101 in a direction substantially orthogonal to a diffraction member of a diffraction grating, $L$ denotes a distance from the X-ray source 101 to the first diffraction grating 102, $Z1$ denotes a distance from the first diffraction grating 102 to the second diffraction grating 103, $Z2$ denotes a distance from the second diffraction grating 103 to the X-ray image detector 105, $m$ denotes an integer, and $d$ denotes a period of diffraction member (a period of diffraction grating, a grating constant, a distance between centers of diffraction members adjacent to each other, or the pitch P).

In the X-ray Talbot interferometer 100A having the above configuration, X-ray is output from the X-ray source 101 toward the first diffraction grating 102. The output X-ray generates a Talbot effect on the first diffraction grating 102, and forms a Talbot image. The Talbot image forms moire fringes (image contrast) while passing through the second grating 103. Then, the image contrast is detected by the X-ray image detector 105.

The Talbot effect is such that an image (a self image of diffraction grating) identical to an image of diffraction grating is formed at a position away from the diffraction grating by a certain distance by incidence of light onto the diffraction grating. The certain distance is called a Talbot distance $L$, and the self image is called a Talbot image. The Talbot distance $L$ is $Z1$ ($L=Z1$) as expressed by the formula 2, in the case where the diffraction grating is a phase-type diffraction grating. The Talbot image is such that a mirror image is generated when the Talbot distance is equal to an odd multiple of $L$ (=(2 m+1) where $L$, $m$ is an integer), and a normal image is generated when the Talbot distance is equal to an even multiple of $L$ (=2 mL).

In the case where a subject S to be detected is disposed between the X-ray source 101 and the first diffraction grating 102, the moire fringes are modulated by the subject S. The modulation amount is proportional to an angle at which X-ray is refracted by refraction effect by the subject S. Accordingly, it is possible to detect the subject S and the inner structure of the subject S by analyzing the moire fringes.

In the Talbot interferometer 100A having the configuration as shown in FIG. 7, the X-ray source 101 is a single spot light source. Such a single spot light source can be configured by additionally providing a single slit plate having a single slit formed therein. X-ray output from the X-ray source 101 passes through the single slit formed in the single slit plate, and is irradiated toward the first diffraction grating 102 via the subject S. The slit is an oblong rectangular opening extending in one direction.

On the other hand, as shown in FIG. 8, a Talbot-Lau interferometer 100B is provided with an X-ray source 101, a multiple slit plate 104, a first diffraction grating 102, and a second diffraction grating 103. Specifically, the Talbot-Lau interferometer 100B is provided with, in addition to the Talbot interferometer 100A shown in FIG. 7, the multiple slit plate 104 having an array of slits formed therein on the X-ray output side of the X-ray source 101.

The multiple slit plate 104 may have a grating structure manufactured by the method for manufacturing a metal grating structure DG according to the embodiment. Manufacturing the multiple slit plate 104 by the method for manufacturing a metal grating structure DG according to the embodiment enables to transmit X-ray through the slits (the second slit parts 12a), and to securely block transmittance of X-ray by the metal parts 12b. Accordingly, it is possible to clearly discriminate between X-ray transmittance and non-transmittance, thereby securely forming a multiple light source device.

As compared with the Talbot interferometer 100A, configuring the Talbot-Lau interferometer 100B increases the amount of X-ray to be irradiated to the first diffraction grating 102 via the subject S. This is more advantageous in obtaining moire fringes in a satisfactory manner.

Some examples of the first diffraction grating 102, the second diffraction grating 103, and the multiple slit plate 104 to be used in the Talbot interferometer 100A or in the Talbot-Lau interferometer 100B are described as follows. It should be noted that in the examples, the first silicon parts 12a and the metal parts 12b are each formed to have a same width, and the metal parts 12b are made of gold.

As an example, in the case where the distance R1 from the X-ray source 101 or from the multiple slit plate 104 to the first diffraction grating 102 is 2 m, and the distance R2 from the X-ray source 101 or from the multiple slit plate 104 to the second diffraction grating 103 is 2.5 m, the pitch P of the first diffraction grating 102 is 5 µm, and the thickness of the metal part 12b thereof is 3 µm; the pitch P of the second diffraction grating 103 is 6 µm, and the thickness of the metal part 12b thereof is 100 µm (aspect ratio=100/3); and the pitch P of the multiple slit plate 104 is 30 µm, and the thickness of the metal part 12b thereof is 100 µm.

As another example, in the case where the distance R1 from the X-ray source 101 or from the multiple slit plate 104 to the first diffraction grating 102 is 1.8 m, and the distance R2 from the X-ray source 101 or from the multiple slit plate 104 to the second diffraction grating 103 is 2:5 m, the pitch P of the first diffraction grating 102 is 7 µm, and the thickness of the metal part 12b thereof is 3 µm; the pitch P of the second diffraction grating 103 is 10 µm, and the thickness of the metal part 12b thereof is 100 µm (aspect ratio=100/5); and the pitch P of the multiple slit plate 104 is 20 µm, and the thickness of the metal part 12b thereof is 100 µm.

(X-Ray Imaging Device)

The metal grating structure DG can be utilized in a variety of optical devices. The metal parts 12b can be formed with a high aspect ratio. Accordingly, for instance, the metal grating structure DG can be appropriately used in an X-ray imaging device. In particular, an X-ray imaging device incorporated with an X-ray Talbot interferometer employs one of the phase contrast methods for obtaining a transmitted image of a subject by handling X-ray as a wave, and by detecting a phase shift in X-ray resulting from transmittance through the subject. The X-ray imaging device has the advantages that sensitivity improvement as high as about 1,000 times of an absorption contrast method for obtaining an image, in which differences in magnitudes of X-ray absorption by a subject are used as contrast, can be expected and that the amount of X-ray radiation can be reduced to one-hundredth or to one-thousandth, for instance. In this embodiment, an X-ray imaging device provided with an X-ray Talbot interferometer incorporated with the aforementioned diffraction grating DG is described.

Figure 9:
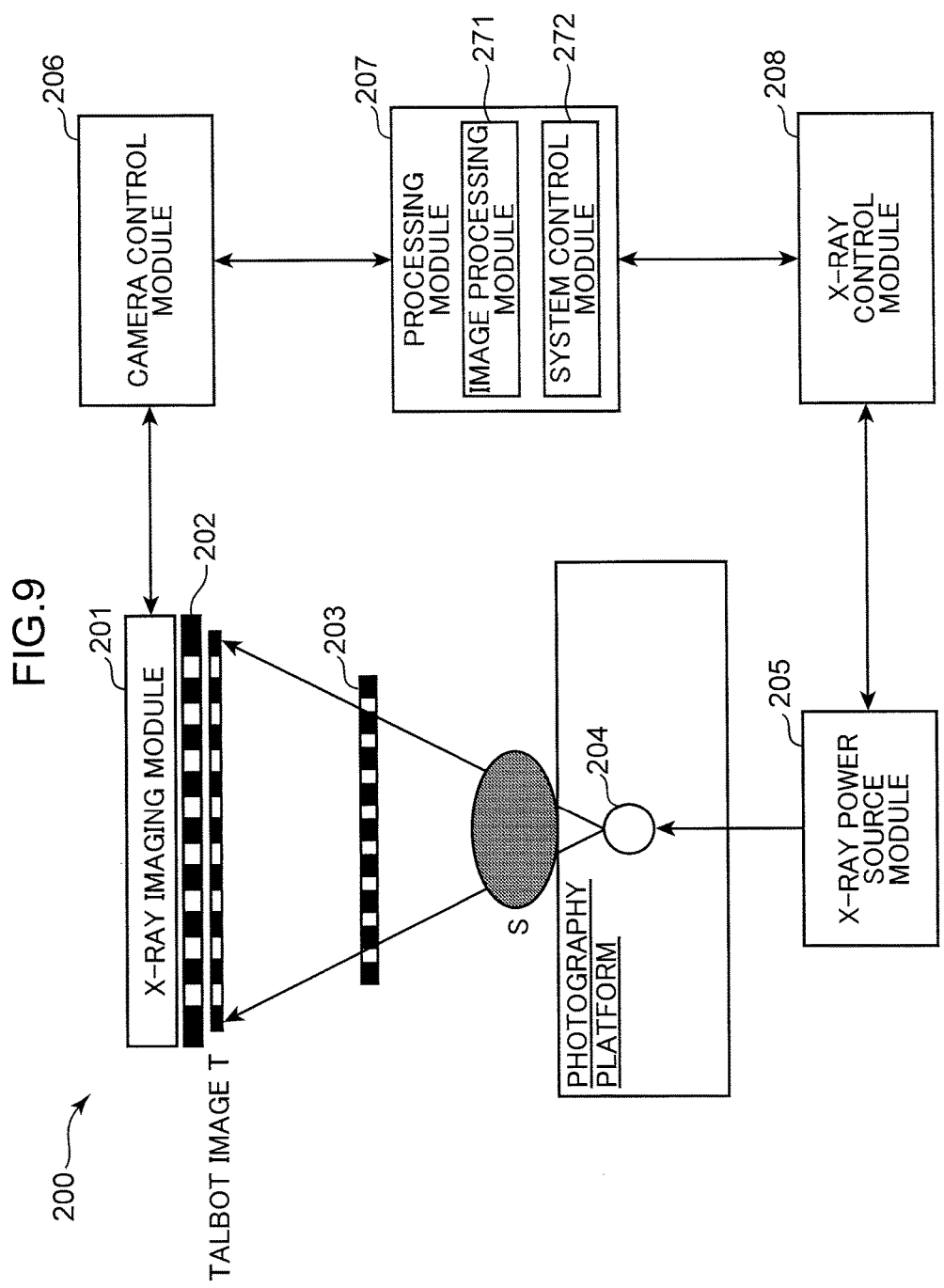
FIG. 9 is an explanatory diagram showing a configuration of an X-ray imaging device according to an embodiment.

FIG. 9 is an explanatory diagram showing a configuration of an X-ray imaging device according to an embodiment. Referring to FIG. 9, an X-ray imaging device 200 is provided with an X-ray imaging module 201, a second diffraction grating 202, a first diffraction grating 203, and an X-ray source 204. The X-ray imaging device 200 according to the embodiment is further provided with an X-ray power source module 205 which supplies electric power to the X-ray source 204, a camera control module 206 which controls an imaging operation of the X-ray imaging module 201, a processing module 207 which controls the overall operation of the X-ray imaging device 200, and an X-ray control module 208 which controls X-ray radiation by the X-ray source 204 by controlling power supply of the X-ray power source module 205.

The X-ray source 204 is a device that outputs X-ray by receiving electric power from the X-ray power source module 205 to irradiate the X-ray toward the first diffraction grating 203. The X-ray source 204 is, for instance, a device that outputs X-ray by application of a high voltage supplied from the X-ray power source module 205 between a cathode and an anode of the X-ray source 204, and by collision of electrons discharged from filaments of the cathode with the anode.

The first diffraction grating 203 is a transmissive diffraction grating that generates a Talbot effect by X-ray output from the X-ray source 204. For instance, the first diffraction grating 203 is a diffraction grating manufactured by the method for manufacturing a metal grating structure DG according to the embodiment. The first diffraction grating 203 is configured to satisfy the conditions that generate a Talbot effect. The first diffraction grating 203 is a diffraction grating with a grating interval sufficiently larger than the wavelength of X-ray output from the X-ray source 204, for instance, a phase-type diffraction grating having a grating constant (period of diffraction grating) d of about twenty times or more of the wavelength of X-ray. The first diffraction grating 203 may be an amplitude-type diffraction grating substantially equivalent to the above.

The second diffraction grating 202 is a transmissive amplitude-type diffraction grating which is disposed at a position away from the first diffraction grating 203 substantially by a Talbot distance L, and which diffracts X-ray diffracted by the first diffraction grating 203. As with the case of the first diffraction grating 203, the second diffraction grating 202 is also a diffraction grating manufactured by the method for manufacturing a metal grating structure DG according to the embodiment.

The first and second diffraction gratings 203 and 202 are configured to satisfy the conditions that define a Talbot interferometer expressed by the aforementioned formulas 1 and 2.

The X-ray imaging module 201 is a device for imaging an image of X-ray diffracted by the second diffraction grating 202. For instance, the X-ray imaging module 201 is a flat panel detector (FPD) provided with a two-dimensional image sensor configured such that a film layer including a scintillator for absorbing X-ray energy and emitting fluorescence is formed on a light receiving surface; or an image intensifier camera provided with an image intensifier module which converts incident photons into electrons on a photoelectric surface, multiplies the electrons by a micro-channel plate, and causes the multiplied electron groups to collide with fluorescent bodies to emit fluorescence, and a two-dimensional image sensor which picks up an image of light output from the image intensifier module.

The processing module 207 is a device for controlling the overall operation of the X-ray imaging device 200 by controlling the respective parts of the X-ray imaging device 200. For instance, the processing module 207 is constituted of a microprocessor and peripheral circuits thereof, and is functionally provided with an image processing module 271 and a system control module 272.

The system control module 272 controls the X-ray source 204 to perform X-ray radiation via the X-ray power source module 205 by sending/receiving a control signal to/from the X-ray control module 208, and controls the X-ray imaging module 201 to perform an imaging operation by sending/receiving a control signal to/from the camera control module 206. X-ray is irradiated toward the subject S under the control of the system control module 272, an image generated by the X-ray radiation is picked up by the X-ray imaging module 201, and an image signal is input to the processing module 207 via the camera control module 206.

The image processing module 271 processes an image signal generated by the X-ray imaging module 201, and an image of the subject S is generated.

In the following, an operation to be performed by the X-ray imaging device according to this embodiment is described. A subject S is disposed between the X-ray source 204 and the first diffraction grating 203 by letting the subject S lie on a photography platform equipped with the X-ray source 204 therein (or on the back surface thereof), for instance. When imaging of the subject S is instructed by an unillustrated operating module by a user (operator) operating the X-ray imaging device 200, the system control module 272 in the processing module 207 outputs a control signal to the X-ray control module 208 for irradiating X-ray toward the subject S. By the control signal, the X-ray control module 208 causes the X-ray power source module 205 to supply electric power to the X-ray source 204, and the X-ray source 204 outputs X-ray to irradiate the X-ray toward the subject S.

The irradiated X-ray passes through the first diffraction grating 203 via the subject S, and is diffracted by the first diffraction grating 203, whereby a Talbot image T as a self image of the first diffraction grating 203 is formed at a position away from the first diffraction grating 203 by a Talbot distance L (=Z1).

The thus-formed Talbot image T i.e. the X-ray is diffracted by the second diffraction grating 202, and an image constituted of moire fringes is formed by generation of moire. The image constituted of moire fringes is picked up by the X-ray imaging module 201 whose exposure time is controlled by the system control module 272, for instance.

The X-ray imaging module 201 outputs an image signal indicative of the image of moire fringes to the processing module 207 via the camera control module 206. The image signal is processed by the image processing module 271 in the processing module 207.

The subject S is disposed between the X-ray source 204 and the first diffraction grating 203. Accordingly, the phase of the X-ray that passes through the subject S is shifted from the phase of the X-ray that does not pass through the subject S. As a result, the X-ray incident to the first diffraction grating 203 includes distortion on a wave front thereof, and the Talbot image T is deformed according to the distortion. The moire fringes of the image generated by overlapping the Talbot image T and the second diffraction grating 202 are modulated by the subject S. The modulation amount is proportional to an angle at which the X-ray is refracted by refraction effect by the subject S. Accordingly, it is possible to detect the subject S and the inner structure of the subject S by analyzing the moire fringes. Further, it is possible to form a tomographic image of the subject S by X-ray computed tomography (CT) by imaging the subject S from different angles.

The second diffraction grating 202 in this embodiment has the metal grating structure DG provided with the metal parts 12b of a high aspect ratio according to the embodiment. Accordingly, it is possible to obtain moire fringes in a satisfactory manner, thereby obtaining an image of the subject S with high precision.

Further, in the metal grating structure DG, the plate like portions 32 (second silicon parts 12a) of the silicon substrate 30 are dry etched by a Bosch process. This makes it possible to form the side surfaces of the slit groove SD into a flat surface, thereby forming the second diffraction grating 202 with high precision. This is advantageous in obtaining moire fringes in a satisfactory manner, thereby obtaining an image of the subject S with high precision.

The aforementioned X-ray imaging device 200 is such that a Talbot interferometer is constituted of the X-ray source 204, the first diffraction grating 203, and the second diffraction grating 202. Alternatively, a Talbot-Lau interferometer may be configured by additionally disposing the metal grating structure DG according to the embodiment as a multiple slit member on the X-ray output side of the X-ray source 204. Configuring such a Talbot-Lau interferometer enables to increase the amount of X-ray to be irradiated to the subject S, as compared with a configuration of disposing a single slit member. This is advantageous in obtaining moire fringes in a satisfactory manner, thereby obtaining an image of the subject S with high precision.

Further, in the aforementioned X-ray imaging device 200, a subject S is disposed between the X-ray source 204 and the first diffraction grating 203. Alternatively, a subject S may be disposed between the first diffraction grating 203 and the second diffraction grating 202.

Further, in the aforementioned X-ray imaging device 200, an image of X-ray is picked up by the X-ray imaging module 201, and electronic data of the image is obtained. Alternatively, an image of X-ray may be picked up by an X-ray film.

The specification discloses the aforementioned features. The following is a summary of the primary features of the embodiment.

A method for manufacturing a metal grating structure according to an aspect includes a resist layer forming step of forming a resist layer on a principal plane of a silicon substrate; a patterning step of patterning the resist layer to remove the patterned portion of the resist layer; an etching step of etching the silicon substrate corresponding to the removed portion of the resist layer by a dry etching method to form a concave portion of a predetermined depth; an insulating layer forming step of forming an insulating layer on an inner surface of the concave portion in the silicon substrate by a thermal oxidation method; a removing step of removing a portion of the insulating layer formed on a bottom portion of the concave portion; and an electroforming step of applying a voltage to the silicon substrate to fill the concave portion with metal by an electroforming method.

In the metal grating structure manufacturing method having the above configuration, a silicon substrate is dry etched. Accordingly, for instance, it is possible to form the concave portion of a high ratio (aspect ratio of the concave portion=depth/width) of depth to width of the concave portion such as a slit groove or a columnar hole. As a result, in the metal grating structure manufacturing method having the above configuration, it is possible to manufacture a metal grating structure having a metal part of a high aspect ratio by filling the concave portion with metal. In filling the concave portion with metal by an electroforming method in the electroforming step, at first, in the insulating layer forming step, an insulating layer is formed on the inner surface of the concave portion by a thermal oxidation method, and then, in the removing step, the bottom portion of the concave portion in the insulating layer is removed. Accordingly, in the insulating layer forming step, the insulating layer is formed by a thermal oxidation method capable of forming a fine film having a high adhesiveness and capable of relatively easily controlling the film thickness. This is advantageous in forming a silicon oxide film ($SiO_2$ film) of a predetermined film thickness capable of securing electrical insulation in an electroforming method in the electroforming step, and is advantageous in insulating, by the insulating layer, a wall surface portion (inner side surface portions of the concave portion) of a wall portion of the silicon substrate that constitutes the concave portion and that remains in the etching step, while making the bottom portion of the concave portion electrically conductive. Accordingly, the metal is securely precipitated and grown on the bottom portion of the concave portion, without precipitating and growing the metal on the wall surface (inner side surfaces) of the concave portion. Thus, the metal grating structure manufacturing method having the above configuration can effectively suppress generation of voids, because the metal is preferentially grown on the bottom portion of the concave portion. Accordingly, the metal grating structure manufacturing method having the above configuration is advantageous in finely forming the metal parts of the grating structure by an electroforming method.

Further, in the metal grating structure manufacturing method having the above configuration, the resist layer may have a thickness larger than a thickness of the insulating layer so that the resist layer remains after the etching step and the removing step.

In the above configuration, the thickness of the resist layer is larger than the thickness of the insulating layer. Accordingly, even in the case where the resist layer is etched and removed by the removing process in the removing step, the resist layer securely remains after the removing step. Thus, the metal grating structure manufacturing method having the above configuration is also advantageous in securing, by the resist layer, an insulating property of the apex portion (upper surface) of the wall portion of the silicon substrate that constitutes the concave portion and that remains after the etching step in the electroforming method.

Further, in the metal grating structure manufacturing method having the above configuration, the resist layer may be made of a material having a resistance against an etching process in the etching step and a removing process in the removing step, the material being different from a material of the insulating layer. In the metal grating structure manufacturing method having the above configuration, preferably, the resist layer may be an alumina film ($Al_2O_3$ film) or an aluminum film (Al film).

In the above configuration, the resist layer is made of a material having a resistance against a removing process in the removing step, the material being different from the material of the insulating layer. Accordingly, it is possible to preferentially remove only the insulating layer in the removing step, and the resist layer remains after the removing step. Thus, the metal grating structure manufacturing method having the above configuration is advantageous in securing an insulating property of a wall portion of the silicon substrate that constitutes the concave portion and that remains after the etching step in the electroforming method.

Further, in the metal grating structure manufacturing method having one of the above configurations, the dry etching method may be RIE (reactive ion etching).

In the metal grating structure manufacturing method having the above configuration, it is possible to perform anisotropic etching by RIE. Accordingly, it is possible to etch the silicon substrate in a depth direction (direction perpendicular to the principal plane (surface)), thereby forming the concave portion relatively easily.

Further, in the metal grating structure manufacturing method having one of the above configurations, the dry etching method may be a Bosch process.

In the metal grating structure manufacturing method having the above configuration, it is possible to dry etch the silicon substrate by the Bosch process. Accordingly, this is advantageous in forming a side surface of the concave portion into a flat shape, thereby forming a metal grating structure with high precision.

Further, in the metal grating structure manufacturing method having one of the above configurations, the silicon substrate may be an n-type silicon substrate.

In the metal grating structure manufacturing method having the above configuration, the electric conductive type of the silicon substrate is n-type. Accordingly, in the case where the silicon substrate is used as a cathode in an electroforming method, it is easy to supply electrons from the silicon substrate to a plating solution, thereby precipitating metal.

Further, the metal grating structure manufacturing method having one of the above configurations is used in manufacturing a metal grating structure for use in an X-ray Talbot interferometer or an X-ray Talbot-Lau interferometer.

As described above, X-ray radiation requires a high aspect ratio. Use of the metal grating structure manufacturing method having one of the configurations enables to manufacture a diffraction grating or a metal grating structure provided with a multiple slit plate for use in an X-ray Talbot interferometer or an X-ray Talbot-Lau interferometer provided with a very fine metal part of a high aspect ratio.

A metal grating structure according to another aspect of the present invention is manufactured by the metal grating structure manufacturing method having one of the above configurations.

The metal grating structure to be manufactured by the metal grating structure manufacturing method having one of the above configurations is provided with a very fine metal part of a high aspect ratio. Accordingly, the metal grating structure having the above configuration can be appropriately used for X-ray devices, for instance, particularly, can be more advantageously used for an X-ray Talbot interferometer or an X-ray Talbot-Lau interferometer.

Further, an X-ray imaging device according to yet another aspect of the present invention includes an X-ray source which outputs an X-ray; a Talbot interferometer or a Talbot-Lau interferometer on which the X-ray output from the X-ray source is irradiated; and an X-ray imaging element which picks up an image of X-ray by the Talbot interferometer or the Talbot-Lau interferometer, wherein the Talbot interferometer or the Talbot-Lau interferometer includes the metal grating structure having the above configuration.

The X-ray imaging device having the above configuration is incorporated with, as a metal grating structure constituting a Talbot interferometer or a Talbot-Lau interferometer, the aforementioned metal grating structure provided with a very fine metal part. This is advantageous in securely diffracting an X-ray, thereby obtaining a clear image of the X-ray.

This application is based on Japanese Patent Application No. 2010-284250 filed on Dec. 21, 2010, the contents of which are hereby incorporated by reference.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

INDUSTRIAL APPLICABILITY

According to the present invention, it is possible to provide a method for manufacturing a metal grating structure appropriately used for, for instance, a Talbot interferometer or a Talbot-Lau interferometer, a metal grating structure manufactured by the manufacturing method, and an X-ray imaging device incorporated with the metal grating structure.

The invention claimed is:

1. A method for manufacturing a metal grating structure, comprising:
    forming a resist layer of one of a silicon oxide film and an alumina film on a principal plane of a silicon substrate;
    patterning the resist layer to remove the patterned portion of the resist layer;
    etching the silicon substrate corresponding to the removed portion of the resist layer to form a concave portion of a predetermined depth;
    forming an insulating layer on an inner surface of the concave portion in the silicon substrate in a single step, with the resist layer remaining on the principal plane, by a thermal oxidation method;
    removing a portion of the insulating layer formed on a bottom portion of the concave portion in a single step; and
    filling the concave portion with metal by an electroforming method with application of a voltage to the silicon substrate,
    wherein the resist layer has a thickness larger than a thickness of the insulating layer so that the resist layer remains after removing the portion of the insulating layer.

2. The method for manufacturing a metal grating structure according to claim 1, wherein the resist layer is a silicon oxide film.

3. The method for manufacturing a metal grating structure according to claim 1, wherein the silicon substrate is etched by RIE (reactive ion etching).

4. The method for manufacturing a metal grating structure according to claim 1, wherein the silicon substrate is etched by a Bosch process.

5. The method for manufacturing a metal grating structure according to claim 1, wherein the silicon substrate is an n-type silicon substrate.

6. The method for manufacturing a metal grating structure according to claim 1, wherein the metal grating structure is a grating for use in an X-ray Talbot interferometer or an X-ray Talbot-Lau interferometer.

7. A metal grating structure manufactured by the method for manufacturing a metal grating structure of claim 1.

8. An X-ray imaging device, comprising:
    an X-ray source which outputs an X-ray;
    a Talbot interferometer or a Talbot-Lau interferometer on which the X-ray output from the X-ray source is irradiated; and
    an X-ray imaging element which picks up an image of X-ray by the Talbot interferometer or the Talbot-Lau interferometer, wherein
    the Talbot interferometer or the Talbot-Lau interferometer includes the metal grating structure of claim 7.

9. The method for manufacturing a metal grating structure according to claim 1, wherein the portion of the insulating layer is removed by a dry etching method.

10. The method for manufacturing a metal grating structure according to claim 1, wherein forming the insulating layer on the inner surface of the concave portion in the silicon substrate further comprises forming the insulating layer on the resist layer.

11. The method for manufacturing a metal grating structure according to claim 1, wherein the resist layer is an alumina film.

12. The method for manufacturing a metal grating structure according to claim 1, comprising:
    forming the insulating layer of a single compound.

13. The method for manufacturing a metal grating structure according to claim 1, comprising:
    forming the insulating layer having a thickness of from several nanometers to about a micron.

14. The method for manufacturing a metal grating structure according to claim 1, comprising:
    forming the insulating layer by a single process.

* * * * *